United States Patent
Knebel

(10) Patent No.: US 10,281,705 B2
(45) Date of Patent: May 7, 2019

(54) METHOD AND DEVICE FOR MICROSCOPIC EXAMINATION OF A SAMPLE

(71) Applicant: LEICA MICROSYSTEMS CMS GMBH, Wetzlar (DE)

(72) Inventor: Werner Knebel, Kronau (DE)

(73) Assignee: LEICA MICROSYSTEMS CMS GMBH, Wetzlar (DE)

(*) Notice: Subject to any disclaimer, the term of this patent is extended or adjusted under 35 U.S.C. 154(b) by 5 days.

(21) Appl. No.: 15/327,391

(22) PCT Filed: Jul. 22, 2015

(86) PCT No.: PCT/EP2015/066799
§ 371 (c)(1),
(2) Date: Jan. 19, 2017

(87) PCT Pub. No.: WO2016/012518
PCT Pub. Date: Jan. 28, 2016

(65) Prior Publication Data
US 2017/0160531 A1    Jun. 8, 2017

(30) Foreign Application Priority Data

Jul. 22, 2014  (LU) .......................................... 92505

(51) Int. Cl.
| G02B 21/16 | (2006.01) |
| G01N 21/64 | (2006.01) |
| G02B 21/06 | (2006.01) |
| G02B 27/56 | (2006.01) |
| G02B 21/00 | (2006.01) |

(52) U.S. Cl.
CPC ............ G02B 21/16 (2013.01); G01N 21/648 (2013.01); G01N 21/6458 (2013.01); G02B 21/002 (2013.01); G02B 21/06 (2013.01); G02B 27/56 (2013.01)

(58) Field of Classification Search
CPC ...... G02B 21/16; G02B 21/002; G02B 21/06; G01N 21/6458; G01N 21/648
See application file for complete search history.

(56) References Cited

U.S. PATENT DOCUMENTS

| 2,844,992 | A | * | 7/1958 | Bernhardt | ............... G02B 21/02 359/387 |
| 4,626,079 | A | * | 12/1986 | Nakamura | ............. G02B 21/10 359/387 |
| 2006/0250689 | A1 | | 11/2006 | Ulrich et al. | |
| 2007/0052958 | A1 | | 3/2007 | Ulrich et al. | |
| 2008/0049313 | A1 | * | 2/2008 | Brehm | ................. G01N 21/648 359/387 |
| 2014/0300958 | A1 | | 10/2014 | Knebel et al. | |
| 2016/0048012 | A1 | | 2/2016 | Knebel et al. | |
| 2016/0153892 | A1 | | 6/2016 | Knebel et al. | |

FOREIGN PATENT DOCUMENTS

| DE | 10344410 A1 | 4/2005 |
| DE | 102005040833 A1 | 3/2007 |
| DE | 102006039976 A1 | 2/2008 |
| WO | WO 2005031429 A1 | 4/2005 |
| WO | WO 2013060644 A1 | 5/2013 |
| WO | WO 2014147207 A1 | 9/2014 |
| WO | WO 2014202704 A1 | 12/2014 |

* cited by examiner

*Primary Examiner* — Michael C Bryant
(74) *Attorney, Agent, or Firm* — Leydig, Voit & Mayer, Ltd.

(57) ABSTRACT

A method for microscopic examination of a specimen includes bringing the specimen into contact with an optically transparent medium that has a higher refractive index than the specimen. An illumination light bundle is generated and directed through an illumination objective that focuses the illumination light bundle. The illumination light bundle that has passed through the illumination objective in the direction of the specimen that is to be examined is deflected using a deflector arranged on a detection objective in such a way that the illumination light bundle strikes a boundary surface between the optically transparent medium and the specimen, where the illumination light bundle is totally reflected for purposes of evanescently illuminating the specimen. Fluorescent light that is emitted by the specimen and that passes through the detection objective is detected.

17 Claims, 10 Drawing Sheets

METHOD AND DEVICE FOR MICROSCOPIC EXAMINATION OF A SAMPLE

CROSS-REFERENCE TO PRIOR APPLICATIONS

This application is a U.S. National Stage Application under 35 U.S.C. § 371 of International Application No. PCT/EP2015/066799 filed on Jul. 22, 2015, and claims benefit to Luxembourg Patent Application No. LU 92505 filed on Jul. 22, 2014. The International Application was published in German on Jan. 28, 2016 as WO 2016/012518 A1 under PCT Article 21(2).

FIELD

The invention relates to a method for the microscopic examination of a specimen.

The invention also relates to a device for carrying out such a method.

BACKGROUND

Within the scope of microscopic fluorescence examinations of specimens, the specimens are usually illuminated directly with an illumination light bundle in order to optically excite the specimen in the illuminated region and to subsequently detect the fluorescent light that is being emitted by the specimen. In scanning microscopy, the focus of an illumination light bundle is directed over or through the specimen in a meandering pattern, generally using a controllable beam deflector that can comprise, for example, one or more tilting mirrors, and in this manner, the specimen is scanned one point at a time.

As an alternative to direct specimen illumination, it is also possible to illuminate the specimen evanescently. Here, the excitation light is totally reflected on a boundary surface to the specimen, whereby the specimen is excited by the evanescent electromagnetic field that diminishes with the penetration depth. The term TIRFM (total internal reflection fluorescence microscopy) has become established for this type of specimen examination.

German patent application DE 103 44 410 A1 discloses a scanning microscope with evanescent specimen illumination. The scanning microscope comprises a light source whose light is coupled into a cover glass so that the light can propagate over the surface of a cover glass through total internal reflection and can illuminate a large surface area of a specimen that is arranged on the cover glass. Moreover, the scanning microscope has a point detector that receives detection light that is emitted by a scanned point of the specimen, and it also has a beam deflector arranged in the beam path of the detection light in order to shift the position of the scanned point in the specimen. However, this device has the drawback that the coupling of the illumination light into the cover glass is not very efficient, as a result of which only a reduced quantity of light is available to evanescently illuminate the specimen.

Moreover, when it comes to the evanescent illumination of specimens, the methods and devices known from the state of the art often have the drawback that the precise location of the specimen illumination cannot be set flexibly and sufficiently precisely.

Moreover, the methods and devices known from the state of the art entail the disadvantage that, prior to a microscopic examination under evanescent illumination, the specimens have to be laboriously arranged and prepared in special specimen chambers or between cover glasses before the specimen chamber or the arrangements of cover glasses between which the specimen is mechanically clamped can be laid onto the object stage of a microscope. It is often the case that precisely the edge regions of the specimen that are located at the boundary surface where the total reflection is supposed to take place are damaged by the continuous pressure stress, so that the subsequent microscopic examination is at the minimum negatively influenced or even rendered completely impossible.

SUMMARY

In an embodiment, the present invention provides a method for microscopic examination of a specimen includes bringing the specimen into contact with an optically transparent medium that has a higher refractive index than the specimen. An illumination light bundle is generated and directed through an illumination objective that focuses the illumination light bundle. The illumination light bundle that has passed through the illumination objective in the direction of the specimen that is to be examined is deflected using a deflector arranged on a detection objective in such a way that the illumination light bundle strikes a boundary surface between the optically transparent medium and the specimen, where the illumination light bundle is totally reflected for purposes of evanescently illuminating the specimen. Fluorescent light that is emitted by the specimen and that passes through the detection objective is detected.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
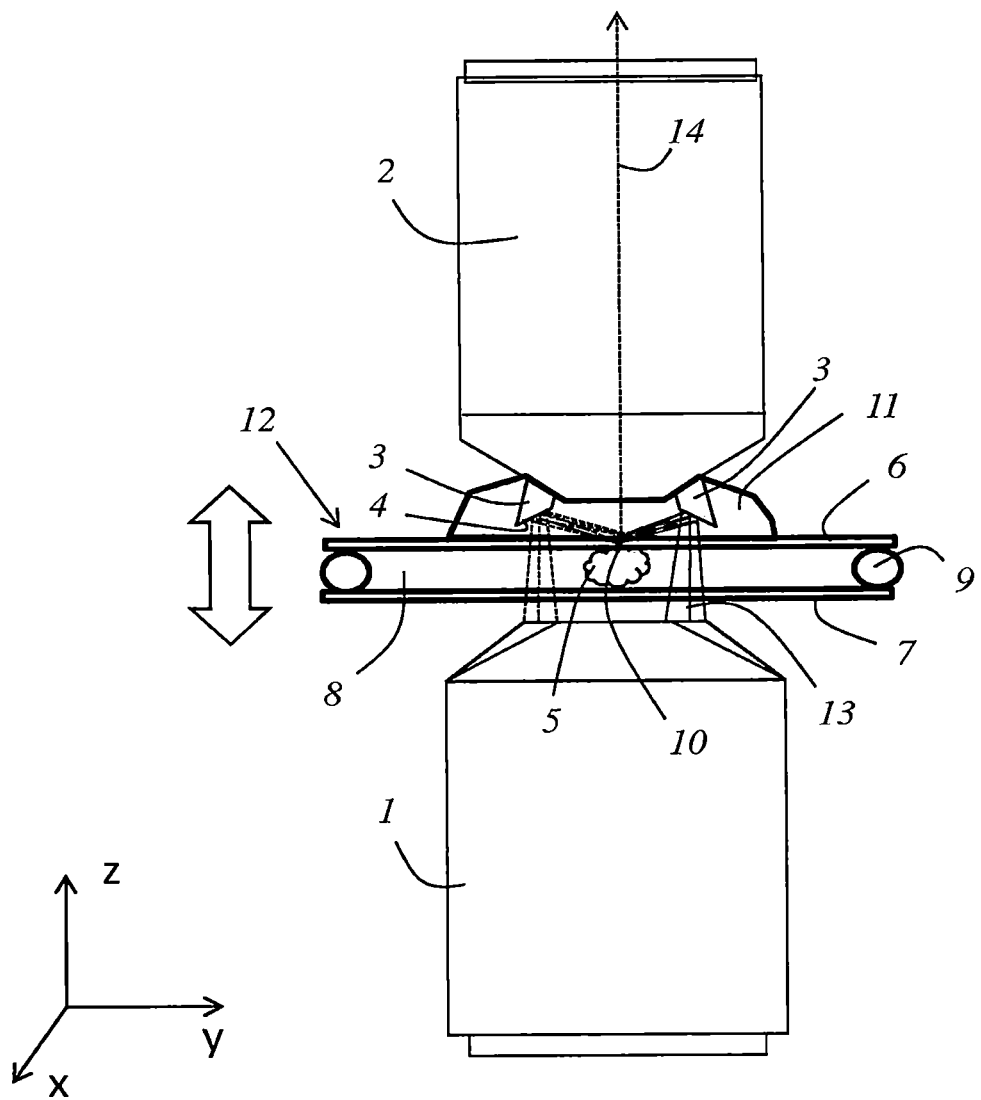
FIG. 1 a detailed view of a first embodiment of a device for carrying out the method according to the invention, with a deflector having a mirror, FIG. 2 a detailed view of a second embodiment of a device for carrying out the method according to the invention, in which the deflector is configured as a block made of a transparent material, FIG. 3 a detailed view of a third embodiment of a device for carrying out the method according to the invention, in which the deflector additionally assumes the function of a front lens of the detection objective, FIG. 4 a detailed view of a fourth embodiment, in which an evanescent specimen illumination as well as a direct specimen illumination are made possible. The set-up for an evanescent specimen illumination is shown.

In an embodiment, the present invention provides a method for the microscopic examination of a specimen that can be used flexibly for different specimens and arrangements of specimens, and especially that can be carried out in a manner that is gentle to the specimens.

According to an embodiment, the method comprises the following steps:
  a. bringing the specimen into contact with an optically transparent medium that has a higher refractive index than the specimen,
  b. generating an illumination light bundle,
  c. directing the illumination light bundle through an illumination objective that focuses the illumination light bundle,
  d. deflecting the illumination light bundle that has passed through the illumination objective in the direction of the specimen that is to be examined, which is done using a deflector arranged on a detection objective in such a way that the illumination light bundle strikes a boundary surface between the optically transparent medium and the specimen, where it is totally reflected for purposes of evanescently illuminating the specimen,
  e. detecting the fluorescent light that is emitted by the specimen and that passes through the detection objective, for instance, using a detector that generates an electric signal that is proportional to the light output of the fluorescent lamp.

In another embodiment, the present invention provides a device that makes it possible to image a microscopic specimen under evanescent illumination using the above-mentioned method.

According to an embodiment, the device has an illumination objective and a detection objective on which a deflector is arranged in order to deflect an illumination light bundle onto a boundary surface between an optically transparent medium and a specimen.

An embodiment of the invention entails the advantage that an evanescent specimen illumination is rendered possible with great efficiency. This can especially be ascribed to the fact that, due to the deflection with the deflector, which takes place after the illumination light bundle has passed through the illumination objective, the illumination light bundle can be easily and reliably directed with the requisite angle of incidence in order to attain a totally internal reflection onto the boundary surface between the optically transparent medium and the specimen.

Moreover, an embodiment of the invention has the additional special advantage that the site of impingement onto the boundary surface between the optically transparent medium and the specimen can be changed easily and without the risk that the critical angle of the total reflection will be inadvertently traversed, which is explained in greater detail below.

Furthermore, the method according to an embodiment of the invention can also be advantageously carried out in such a way that a specimen can be placed into an examination position without any pressure stress at all on the edge region that is to be examined, and so that it is not brought into contact with the optically transparent medium until immediately before a microscopic image is generated, as a result of which the microscopic examination of a virtually unstressed specimen is rendered possible. This is likewise explained in greater detail below, particularly in conjunction with several embodiments.

In order for the illumination light bundle to be reliably oriented with the angle of incidence required for a total internal reflection and for it to strike the boundary surface between the specimen and the optically transparent medium, the boundary surface is preferably oriented at an angle that differs from zero relative to the optical axis of the illumination objective and/or of the detection objective. An embodiment that can be employed in an especially flexible and versatile manner is one in which the boundary surface between the specimen and the optically transparent medium is oriented perpendicular to the optical axis of the illumination objective and/or of the detection objective. In particular, such an orientation makes it possible to illuminate the specimen and especially one and the same specimen region from different directions and especially with the same angle of incidence each time. This is done, for instance, in order to examine the fluorescence properties of the specimen as a function of the polarization of the illumination light, especially as a function of the orientation of the plane of the linear polarization of the illumination light.

In particular, for this purpose, it can be advantageously provided that, after the illumination light bundle has been deflected, it runs in a plane whose angle differs from zero relative to the optical axis of the illumination objective. For example, it can be provided for the illumination light bundle to be deflected in such a way that it strikes the boundary surface between the specimen and the optically transparent medium at an angle of incidence within the range from 55° to 70°, especially in the range from 60° to 64°. Within these ranges, it is possible to achieve an evanescent specimen illumination of most biological specimens with a sufficient penetration depth.

In an especially advantageous embodiment of the method according to the invention, the site of impingement and/or the angle of incidence and/or the direction of incidence of the illumination light bundle onto the boundary surface between the specimen and the optically transparent medium are changed during the microscopic examination.

Changing the site of impingement makes it possible, for example, to consecutively illuminate and examine different specimen regions in that the fluorescent light emitted by these specimen regions is sent to a surface detector such as, for example, a CCD detector, so that a two-dimensional image can be acquired, a process in which an image of each specific specimen region is generated. In particular, it is possible, for example, to systematically scan the edge surface of the specimen that is in contact with the optically transparent medium along a scanning path and to associate each of the scanned specimen regions with a surface image. From the acquired image information, a total image of the specimen can be then be reconstructed for the individual specimen regions. For instance, the site of impingement of the illumination light bundle on the boundary surface between the specimen and the optically transparent medium can be continuously changed along a scanning path, especially one that has a meandering course. In this way, it is possible to do justice to the fact that, as a rule, the illuminated surface area is smaller than the viewing field of the detection objective. The entire viewing field of the detection objective can be utilized by lining up several images of different specimen regions.

However, such an approach is actually reserved for special applications, whereas usually only a sufficiently large illumination focus is generated so that the entire specimen regions of interest can be simultaneously illuminated evanescently and so that an image of the specimen region can be simultaneously generated by a surface detector such as, for example, a CCD detector, so that a two-dimensional image can be acquired.

In order to attain the largest possible illumination spot, the focus of the illumination light bundle should be as long as possible in the direction of propagation of the illumination light and it should have the largest possible focus diameter. A long focus in the direction of propagation of the illumination light is important because the illumination spot on the boundary surface between the optically transparent medium and the specimen is elongated due to the large angle of incidence at which the illumination light bundle strikes the boundary surface. In case of a circular illumination light bundle whose cross section is perpendicular to the direction of propagation, the impingement surface on the boundary surface between the optically transparent medium and the specimen is elliptical by nature. Thus, the focus length should preferably be greater than twice the large semi-axis of the ellipse of the impingement surface. A large focus diameter has an especially great effect in the direction of the small semi-axes.

In order to be able to generate the largest possible focus diameter and the longest possible focus in the direction of propagation, the illumination objective preferably has a small numerical aperture of, for example, 0.05. As merely an approximation and depending on other parameters such as the selected angle of incidence relative to the boundary surface between the optically transparent medium and the specimen, such an objective could illuminate a impingement surface amounting to approximately 100 μm by 10 μm.

In order to attain an enlargement of the impingement surface, especially in the direction of the small semi-axes, it is also possible, instead of a circular illumination light bundle, for an appropriately oriented strip of light, that is to say, an elongated illumination light bundle whose cross section is perpendicular to the direction of propagation, or else a quasi-strip of light, to be coupled into the illumination objective, which is explained in greater detail below.

In a special embodiment, as an alternative or in addition to a change in the site of impingement, a change is made to the angle of incidence of the illumination light bundle onto the boundary surface between the specimen and the optically transparent medium. In this manner, it is possible, for example, to vary the penetration depth of the evanescent field into the specimen and/or the size of the spot that is illuminated by the illumination light bundle.

As an alternative or in addition to a change in the site of impingement and/or to a change in the angle of incidence, it is possible to change the direction of incidence of the illumination light bundle onto the boundary surface between the specimen and the optically transparent medium. This can especially be done so that, along with the direction of incidence, the linear polarization direction of the light striking the boundary surface can also be simultaneously rotated if, for instance, specimen properties that are dependent on the direction of linear polarization are to be examined.

In order to be able to change the site of impingement and/or the angle of incidence and/or the direction of incidence of the illumination light bundle onto the boundary surface between the specimen and the optically transparent medium, it is especially possible to employ a beam deflector that is adjustable in terms of the deflection angle. This beam deflector can comprise, for example, a cardanically suspended tilting mirror or two tilting mirrors that can be rotated around different axes of rotation. In particular, it can be provided for the beam deflector to move the illumination light bundle relative to the illumination objective and/or to the deflector.

As an alternative or in addition to the use of an adjustable beam deflector, it is also possible for the site of impingement and/or the angle of incidence and/or the direction of incidence of the illumination light bundle onto the boundary surface between the specimen and the optically transparent medium to be changed by moving the specimen relative to the illumination objective and/or relative to the illumination light bundle. For this purpose, in particular, an object stage can be used that can preferably be moved in three spatial directions.

Aside from the above-mentioned possibilities for changing the site of impingement, the angle of incidence and/or the direction of incidence, it is also possible to change these parameters by moving the deflector relative to the specimen. This can be done as an alternative or in addition to the use of a beam deflector and/or as an alternative or in addition to moving the specimen. In a special embodiment, the deflector is immovably attached to the detection objective. In particular, in order to nevertheless be able to change the site of impingement and/or the angle of incidence and/or the direction of incidence, the deflector can advantageously be arranged on the detection objective, especially attached thereto.

In a special embodiment, the deflector is arranged in the front area and/or near the front lens.

In a special embodiment, the deflector is configured as a mirror with multiple facets. In particular, such an embodiment makes it possible to change the site of impingement and/or the angle of incidence and/or the direction of incidence of the illumination light bundle onto the boundary surface between the specimen and the optically transparent medium in that different facets are illuminated consecutively, for instance, by an adjustable beam deflector or by moving the deflector. Here, it can especially be provided for the facets to be spatially oriented differently so as to attain a reflection in a different spatial direction in each case. As an alternative, for example, it is also possible for the deflector to have a frusto-conical mirror surface. Such an embodiment makes it possible to rotate the illumination light bundle continuously and around an axis that runs through the site of impingement so as to describe a conical surface.

As explained, the method according to the invention offers numerous possibilities for setting the site of impingement and/or the angle of incidence and/or the direction of incidence, which entails the very special advantage that the user can adapt the method individually to the specimen-specific or examination-specific requirements.

If the site of impingement is changed, especially if the boundary surface between the optically transparent medium and the specimen is being scanned, the specific site of impingement can be associated in each case with a specimen region in order to generate a total image made up of several images.

In particular, it can be provided for an associated specimen region to be determined for each site of impingement, taking into account the angle of incidence and/or the refractive index of the specimen and/or the refractive index of the optically transparent medium and/or the wavelength of the illumination light bundle and/or the diameter of the site of impingement. Within the scope of such a determination, errors, especially system-related errors, are preferably corrected or compensated for. In particular, it is possible to undertake a compensation or correction of spatial deviations of the actual course of the illumination light bundle relative to a beam path that can be expected on the basis of the principles of geometric optics such as, for example, the Goos-Hähnchen effect.

Preferably, a compensation or a correction is also undertaken of the errors that would be caused by a deviation in the thickness of the optically transparent medium, especially a cover glass, from a setpoint thickness. For example, it is not rare for the actual thickness of a cover glass to deviate considerably from the standard thickness of at least 170 µm. Such compensations and the application of such correction factors have the advantage that a particularly good resolution of the image of the specimen that is to be examined can be achieved.

In an advantageous embodiment, at least one specific, especially two-dimensional image—which was acquired by the detection of the detection light emitted by the specimen during the illumination of each specific site of impingement—is associated with each site of impingement and/or with each associated specimen region.

The term "image" refers especially to a reproduction of the specimen or a part of the specimen in the form of data that can be displayed, for example, on a PC and/or in the form of an image that is visible to the naked eye.

The detector can especially be configured in such a way that, for each pixel, it generates an electric signal that is proportional to the light output of the received detection light. In particular, it can also be provided that the detector simultaneously or sequentially receives specific fluorescent light of different wavelengths and, in each case, generates corresponding electric detection signals. For example, the detector can be a CMOS sensor that, as a function of the wavelength, is able to detect fluorescent light in different layers (channels) independently of each other. As an alternative, the detector can comprise several CCD detectors to each of which detection light of different wavelength ranges is fed by dichroic beam splitters. Particularly for a detection of fluorescent light of different wavelengths, the excitation light bundle can comprise several excitation light wavelengths, for example, of a polychromatic laser or of several individual lasers or of a white light source.

As already mentioned, the cross section of the illumination light bundle can be circular. With such an embodiment, the site of impingement onto the boundary surface between the optically transparent medium and the specimen is elongated and elliptical by nature. However, as already mentioned, it is also possible for the illumination light bundle to be in the form of a strip of light. Such a beam form can be achieved, for example, with a cylindrical optical system arranged in the beam path of the illumination light bundle. As an alternative, it is also possible to generate a quasi-strip of light in that a beam deflector is used to move an illumination light bundle with an essentially round cross section back and forth in one spatial direction so quickly that it can no longer be distinguished from a strip of light generated by a cylindrical optical system.

The use of an illumination light bundle in the form of a strip of light makes it possible to illuminate the boundary surface between the optically transparent medium and the specimen over a large surface area.

An arrangement for carrying out the method according to the invention that is very flexible to use and that functions very precisely is obtained when the optical axis of the illumination objective and the optical axis of the detection objective are oriented parallel or coaxially to each other, whereby preferably the detection objective and the illumination objective are facing each other with their front lenses. With such an embodiment, the specimen that is to be examined can be arranged in the space between the illumination objective and the detection objective, whereby advantageously, a great deal of space remains to guide and direct the illumination light bundle, especially for purposes of achieving an illumination of the boundary surface from different directions or with different angles of incidence. This has the special advantage that a plurality of possibilities exists for adapting the examination conditions to the specific requirements.

In an especially advantageous embodiment of the method according to the invention, the same specimen is examined with the same device but a different examination method. Such an approach has the very special advantage that information about the specimen can be obtained with different examination methods, independently of each other, for example, in order to compare these pieces of information to each other or in order to collect as much information about the specimen as possible. Here, the specimen preferably remains in the space between the illumination objective and the detection objective.

In addition to an examination in which, as described above, the specimen is evanescently illuminated, a SPIM examination (Single Plane Illumination Microscopy) can advantageously be carried out in which the illumination light bundle, especially in the form of a strip of light or a quasi-strip of light, is directed onto and through the specimen directly and without total reflection. Such a strip of light or quasi-strip of light completely transilluminates a layer of the specimen, whereby the detection light that is perpendicularly emitted by this layer and collimated by the detection objective is detected. In order to be able to receive location information pertaining to the individual specimen locations on the layer, a surface detector such as, for instance, a CCD detector is preferably used. Through successive shifting of the strip of light relative to the specimen, one layer after another can be transilluminated and a layer stack of space-resolved detection signals and thus a three-dimensional reconstruction of the specimen can be generated.

Particularly for a SPIM examination, it can advantageously be provided that, after the illumination light bundle has passed through the illumination objective, it is deflected directly onto the specimen by another deflector arranged on the illumination objective. This is preferably done in such a way that the strip of light propagates at an angle that differs from zero relative to the optical axis of the detection objective, especially at an angle of 90° relative to the optical axis of the detection objective. Preferably, the plane in which the deflected strip of light or quasi-strip of light propagates is oriented perpendicular to the optical axis of the detection objective. Such an orientation permits a very precise image reconstruction in which the laborious geometric correction computations are largely avoided.

In a special embodiment, at least two deflector are arranged on the detection objective, one of which serves to deflect the illumination light bundle for purposes of evanescently illuminating the specimen, whereas the other deflector serves to deflect the illumination light bundle, which has especially been shaped into a strip of light or quasi-strip of light for purposes of a SPIM examination.

In order to be able to switch back and forth between an evanescent specimen illumination and a direct specimen illumination, the deflector can be arranged movably on the detection objective in such a way that, as desired, either the one deflector or the other deflector can be introduced into the beam path of the illumination light bundle. As an alternative or in addition, it is also possible to direct the illumination light bundle onto the specifically envisaged deflector by using a beam deflector that is adjustable in terms of the deflection angle.

It is usually advantageous for the illumination light bundle to be coupled into the illumination objective in such a way that it runs off-center through the illumination objective, since such a beam path makes it possible to position the specimen onto or at least near the optical axis of the illumination objective and/or of the detection objective, whereby it is ensured that the specimen can be illuminated from very different directions.

With a very special embodiment of a device that is suitable for carrying out the method according to the invention, the optically transparent medium itself is the deflector or at least part of the deflector. In particular, such an embodiment makes it possible to first position the specimen between the illumination objective and the detection objective in such a way that it is mechanically completely unstressed, for example, in a water-filled Petri dish, whereby the illumination objective is preferably arranged in an inverse microscope arrangement spatially below the specimen, whereas the detection objective is situated above the specimen. In such an arrangement, only immediately before the actual examination can the optically transparent medium be moved—together with the detection objective—to such an extent in the direction of the specimen until it is in contact with the specimen, thereby fulfilling the prerequisite for an evanescent specimen illumination. In this manner, it is effectively prevented that the specimen is subject to pressure stress already a long time before the actual examination, for example, in that it is clamped between cover glasses, as a result of which lasting damage can occur precisely to the edge regions of the specimen that are to be examined, which is an enormous drawback, especially in the case of living specimens.

The deflector can especially have a block made of transparent material, particularly a prism. Here, for example, it can be provided that the illumination light bundle being emitted from the illumination objective is coupled into the prism through a hypotenuse surface of the prism and is reflected on a reflective short face of the prism towards the specimen, which is in contact with the hypotenuse surface, in such a way that the illumination light bundle is totally reflected on the hypotenuse surface as the boundary surface to the specimen. The fluorescent light emitted by the specimen runs through the prism to the detection objective, which then collimates the detection light.

Between the optically transparent medium which, as mentioned, can be made up, for instance, of a block made of transparent material, and the detection objective, there is preferably a means for adapting the refractive indices such as, for example, an immersion oil.

Such an arrangement especially makes it possible to move the detection objective relative to the specimen and relative to the adjacent block made of transparent material, for which purpose there can be an appropriate adjustment means for setting the distance of the block made of transparent material relative to the detection objective. Such an adjustment capability, for example, with a threaded drive, has the advantage that effects such as, for instance, the Goos-Hähnchen effect, that occur during the evanescent illumination, can be compensated for.

In another advantageous embodiment, the optically transparent medium, which simultaneously functions as a deflector, is coupled, especially directly, to a front lens of the detection objective. The coupling can be achieved, for example, using an optical kit between the front lens of the detection objective and the mating block made of transparent material. For example, the front lens can be configured as a hemispherical lens onto which a mating block having with a hemispherical concave coupling surface is coupled, for instance, by means of an optical kit. As an alternative, it can also be provided for the optically transparent medium, which simultaneously functions as a deflector, to comprise a front lens of the detection objective and/or for the deflector to function as the front lens of the detection objective. These solutions have the very special advantage that it is possible to avoid or at least minimize losses of detection light due to undesired reflections on the light path of the detection light via the optically transparent medium and the front lens of the detection objective.

As already mentioned, it can advantageously be provided that the deflector has a block made of transparent material, whereby at least one outer surface of the block, especially the outer surface of the block that is configured and arranged so as to be in contact with a specimen, functions as a window for coupling in the illumination light bundle.

As likewise already mentioned, it can be provided that another outer surface of the block is preferably configured as a mirror or has a mirror in order to deflect the illumination light bundle. As already mentioned, especially for an examination of the same specimen employing a different examination method, another deflector for deflecting the illumination light bundle, especially an illumination light bundle in the form of a strip of light or quasi-strip of light can be present, especially arranged on the detection objective. In particular, the one deflector and/or the other deflector can be movably attached to the detection objective, for example, in order to be able to change the site of impingement and/or the angle of incidence and/or the direction of incidence of the illumination light bundle and/or in order to be able to make geometric corrections, for example, in order to correct the Goos-Hähnchen effect. Particularly for these purposes, as already mentioned, the device for carrying out the method according to the invention can have a beam deflector that is adjustable in terms of the deflection angle.

In particular, the beam deflector can also be a beam deflection means of a scanning microscope, especially a confocal scanning microscope.

A device that is suitable for carrying out the method according to the invention can advantageously be structured on the basis of a scanning microscope, especially a confocal scanning microscope. Here, it especially lends itself to use an inverse microscope stand. Thus, it is especially advantageous to use a scanning microscope (which might already be available in a laboratory anyway) in order to carry out the method according to the invention.

FIG. 1 shows a detailed view of a first embodiment of a device, on the basis of which a conceivable embodiment of the method according to the invention will be explained below.

The device has an illumination objective 1 and a detection objective 2, which is configured as an oil objective. The illumination objective 1 and the detection objective 2 are coaxial to each other in terms of their optical axes and they face in opposite directions. A deflector 3 is attached to the detection objective 2 and it has a frusto-conical mirror surface 4.

The specimen 5 that is to be examined is arranged in an aqueous nutrient medium between a first cover glass 6 and a second cover glass 7. The cover glasses 6, 7 are sealed off with respect to each other by an encircling gasket 9 so that the aqueous nutrient medium 8 cannot escape.

Between the cover glass 6, which is facing the detection objective 2, and the detection objective 2, there is immersion oil 11 into which the deflector 3 is also immersed.

The cover glass 6, which is facing the detection objective 2, serves as an optically transparent medium 12 that has a higher refractive index than the specimen 5. An illumination light bundle 13 is focused by the illumination objective 1 and, after having exited from the front lens of the illumination objective 1, it passes through the cover glasses 6, 7 without interacting with the specimen 5, and ultimately reaches the deflector 3. The deflector 3 then deflects the illumination light bundle 13 in the direction of the specimen 5 that is to be examined, and this is done in such a way that the illumination light bundle 13 strikes the boundary surface 10 between the optically transparent medium 12 and the specimen 5, where it is totally reflected for purposes of evanescently illuminating the specimen 5.

The fluorescent light 14 emitted by the specimen 5 passes through the detection objective 2 and subsequently reaches a surface detector such as, for example, a CCD detector, so that a two-dimensional image can be acquired. A beam deflector can direct the illumination light bundle 13 at different positions of the frusto-conical mirror surface 4 in order to direct the illumination light bundle 13 from different directions of incidence onto the boundary surface 10 between the optically transparent medium 12 and the specimen 5. In the figure, this is only schematically indicated by a broken line showing the changed beam path of the illumination light bundle 13.

Especially in order to achieve a good resolution, it is important for the focus of the illumination light bundle 13 to be precisely on the boundary surface 10 between the optically transparent medium 12 and the specimen 5, especially taking geometric corrections into account such as, for instance, in order to compensate for the Goos-Hähnchen effect or in order to compensate for a deviation in the thickness of the optically transparent medium 12, especially the cover glass 6, from a setpoint thickness. In order to set this precisely, the cover glasses 6, 7, together with the specimen 5, can be adjusted relative to the illumination objective 1 in the Z-direction. For this purpose, for example, a translation stage that is adjustable in the Z-direction can be used.

Moreover, it is also possible for the cover glasses 6, 7, together with the specimen 5 that is placed between them, to be moved in the X-direction and/or in the Y-direction so that the site of impingement of the illumination light bundle 13 onto the boundary surface 10 can be selected. As an alternative or in addition, the site of impingement and/or the angle of incidence and/or the direction of incidence can also be changed by the beam deflector that is adjustable in terms of the deflection angle.

Particularly in order to ensure that the numerical aperture of the detection objective 2 is also utilized to collect the detection light 14, the detection objective 2 can likewise be adjusted in the Z-direction and/or in the X-Y-direction relative to the specimen.

Figure 2:
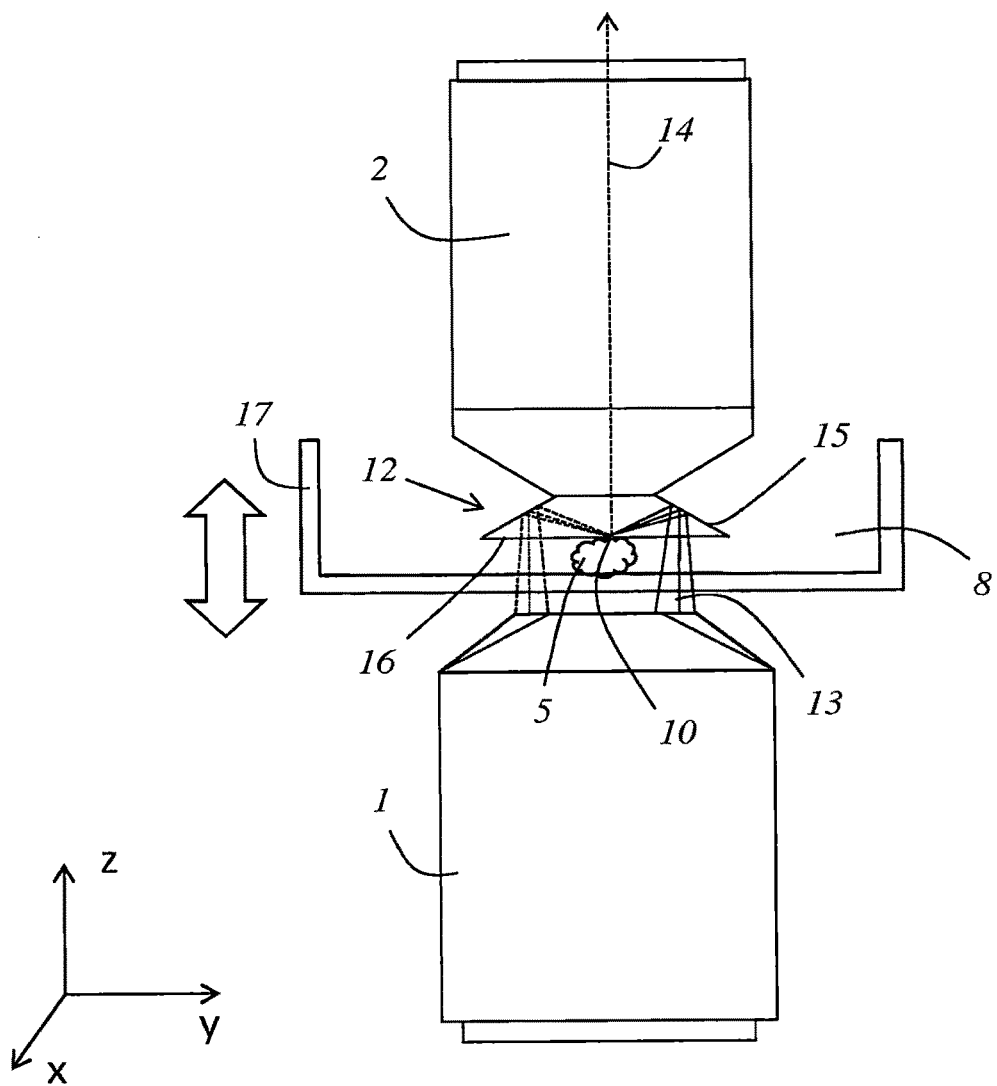

FIG. 2 shows a detailed view of a second embodiment in which the optically transparent medium 12 is configured as a prism that has a reflective surface 15 to deflect the illumination light bundle 13 coming from the illumination objective 1 as well as an outer surface 16 that is configured and arranged so as to come into contact with a specimen 5, so that a boundary surface 10 is formed between the outer surface 16 and the specimen 5 for purposes of the total internal reflection of the illumination light bundle 13.

The specimen 5 is arranged in a vessel 17 that is filled with an aqueous nutrient medium 8 and that is open towards the detection objective 2. Such an embodiment has the very special advantage that the specimen 5 only comes into contact with the optically transparent medium 12 immediately before the actual examination, so that only then is it subject to pressure stress. This avoids or at least greatly diminishes damage to the specimen 5 stemming from continuous pressure stress before the actual examination.

As is the case with the embodiment shown in FIG. 1, the detection light 14 passes through the detection objective 2 to a surface detector such as, for example, a CCD detector, so that a two-dimensional image can be acquired.

In the embodiment shown in FIG. 2, it is also possible, for example, to use a beam deflector that is adjustable in terms of the deflection angle, to flexibly adjust the site of impingement and/or the angle of incidence and/or the direction of incidence of the illumination light bundle 13 onto the boundary surface 10 between the specimen 5 and the optically transparent medium 12, taking into account the examination in question.

In this embodiment, the optically transparent medium 12 is directly coupled to the front lens of the detection objective 2, for example, by means of an optical kit or an immersion oil. In order to examine the specimen 5, the optically transparent medium 12 is immersed into water 8 and placed onto the specimen 5.

Figure 3:
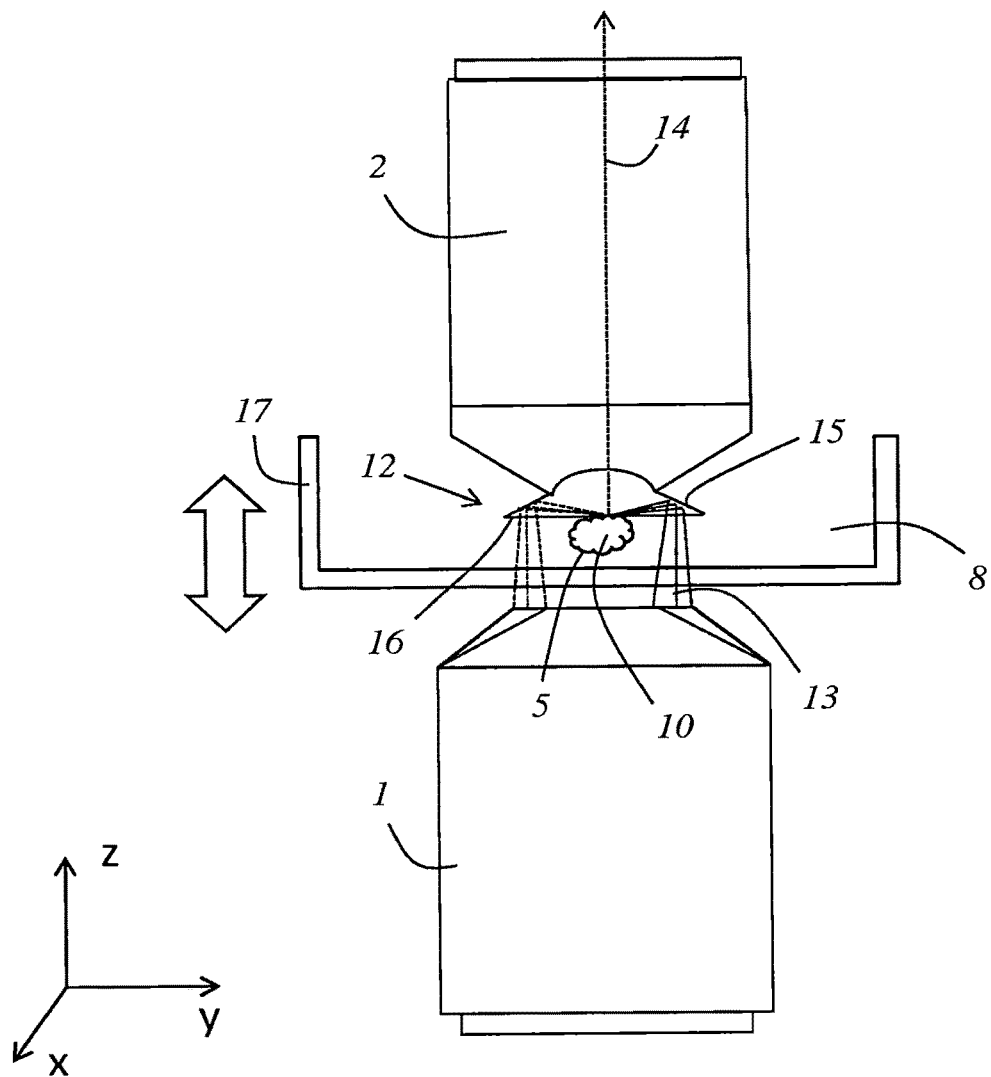

FIG. 3 shows a detailed view of a third embodiment that differs from the embodiment shown in FIG. 2 in that the optically transparent medium 12 is configured in such a way that it can additionally assume the function of the front lens of the detection objective 2. In particular, the optically transparent medium 12 can comprise a front lens and a block that functions as the deflector and that has an outer surface for placement onto the specimen 5, both of which are made in one piece and together. Such an embodiment is very sturdy and not very error-prone.

Figure 4:
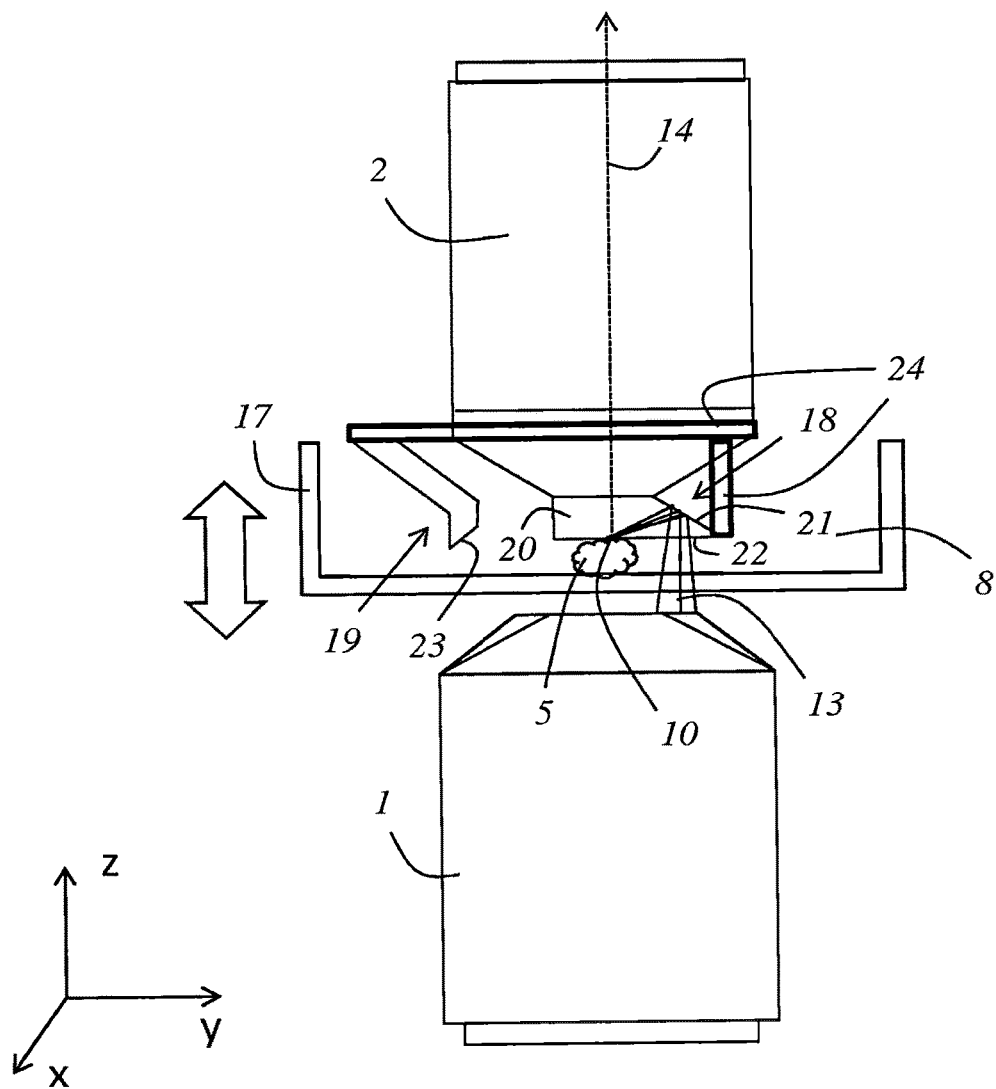
Figure 5:
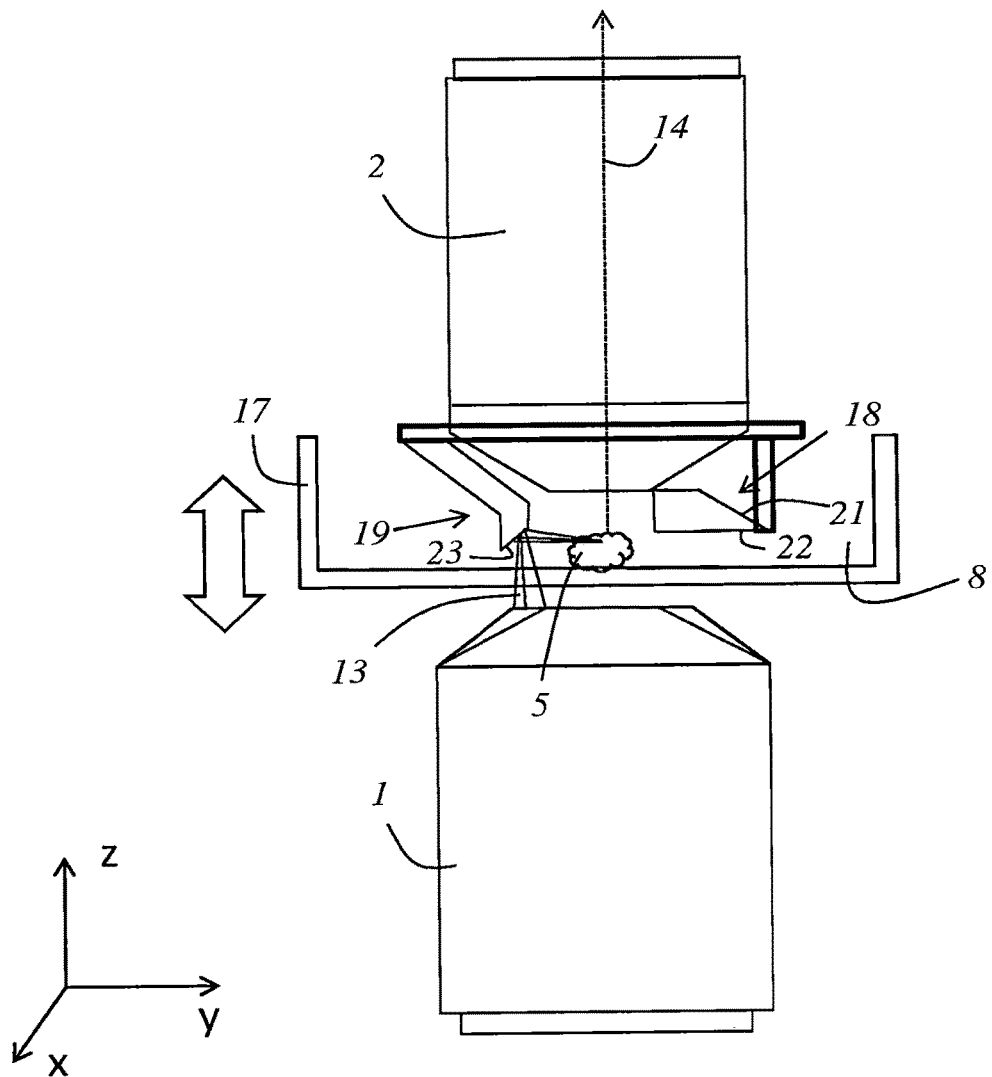
FIG. 5 the detailed view of the fourth embodiment, in the set-up for a direct specimen illumination light bundle for purposes of a SPIM examination, FIGS. 6a and 6b a schematic depiction showing the impingement surface of the illumination light bundle, FIGS. 7a and 7b a schematic depiction showing the change of the site of impingement of the illumination light bundle, FIG. 8 a detailed view of an embodiment with a deflector that has a facet mirror, FIG. 9 a detailed view of an embodiment with a deflector that has a frusto-conical mirror, and FIG. 10 a detailed view of an embodiment with a beam deflector for changing the site of impingement and/or the angle of incidence and/or the direction of incidence.

FIGS. 4 and 5 each show a detailed view of a fourth embodiment of a device for carrying out a method according to the invention. The device has a first deflector 18 and another deflector 19. The first deflector 18 as well as the other deflector 19 are attached to the detection objective 2. The first deflector 18 exhaustively an optically transparent medium 20 that has a reflective surface 21 for deflecting an illumination light bundle 13. Moreover, the optically transparent medium 20 also has an outer surface 22 that is configured and arranged so as to come into contact with a specimen 5 in order to form a boundary surface 10 so as to attain a totally internal reflection.

FIG. 4 shows one of the two possible settings of the device, namely, the setting for carrying out an examination with evanescent specimen illumination. With this setting as well, as described comprehensively above, a change can be made in the site of impingement and/or the angle of incidence and/or the direction of incidence of the illumination light bundle 13 onto the boundary surface 10.

The device is additionally configured to carry out an examination of the same specimen 5 by means of a different examination method such as especially SPIM. For this purpose, the illumination light bundle 13, especially in the form of a strip of light or a quasi-strip of light is directed at the other deflector 19. The other deflector 19 has a second mirror surface 23.

The other deflector 19 deflects the illumination light bundle 13 in such a way that, after the deflection, it propagates in a plane that is perpendicular to the optical axis of the detection objective 2. In this manner, a layer of the specimen 5 is transilluminated and the detection light 14 that is emitted by the specimen and that passes through the detection objective 2 is detected, preferably space-resolved. A surface detector such as, for example, especially a CCD detector or an SCMOS detector, can serve to perform a space-resolved detection of the detection light 14 emitted by the specimen 5, so that a two-dimensional image can be acquired.

In order to set a correct focus position and/or to compensate for special geometric effects of the type that can occur especially with an evanescent specimen illumination, the first deflector 18 and the other deflector 19 are attached to the detection objective 2 so as to be movable and adjustable in terms of their relative position to the detection objective 2. An adjustable attachment means 24 serves for this purpose.

In this embodiment as well, it is advantageous if the individual components can be adjusted relative to each other in terms of their spatial position, for example, in order to correctly set the focus position and/or to set the site of impingement and/or the angle of incidence and/or the direction of incidence.

Figure 6A:
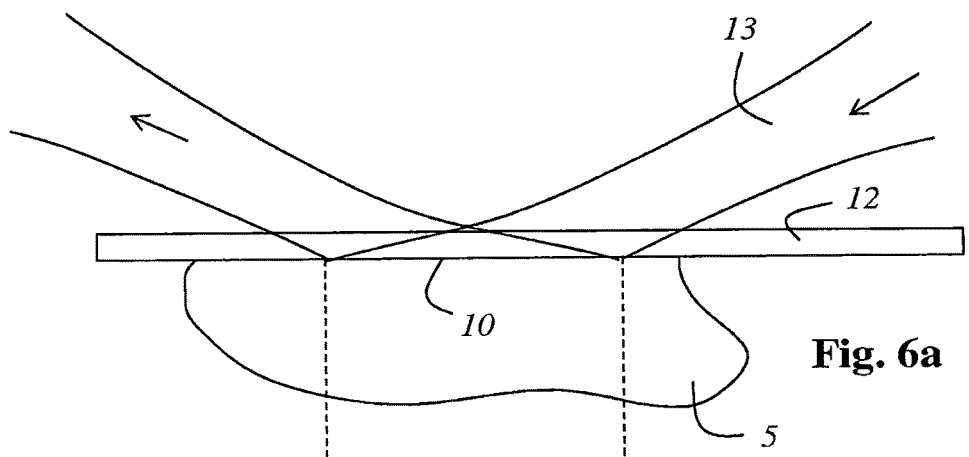
Figure 6B:
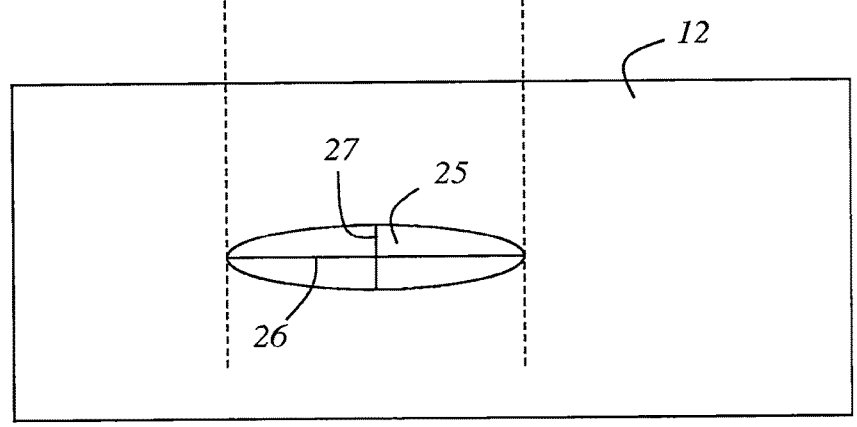

FIGS. 6a and 6b show a schematic depiction of the impingement surface 25 of the illumination light bundle 13 onto the boundary surface 10 between the optically transparent medium 12 and the specimen 5, for an evanescent specimen illumination.

In order to attain the largest possible illumination spot 25, the focus of the illumination light bundle 13 is as long as possible in the direction of propagation of the illumination light and it has a large focus diameter. In case of a circular illumination light bundle whose cross section is perpendicular to the direction of propagation, the impingement surface 25 on the boundary surface 10 between the optically transparent medium 12 and the specimen 5 is elliptical by nature. Thus, the focus length should preferably be greater than twice the large semi-axis 26 of the ellipse of the impingement surface 25, especially by using an illumination objective 1 with a low numerical aperture. The focus diameter corresponds to approximately twice the small semi-axis 27 of the elliptical impingement surface 25. In this direction, an enlargement of the impingement surface 25 can be achieved by using an illumination light bundle 13 in the form of a strip of light or a quasi-strip of light instead of an illumination light bundle 13 with a circular cross section.

Figures 7A, 7B:
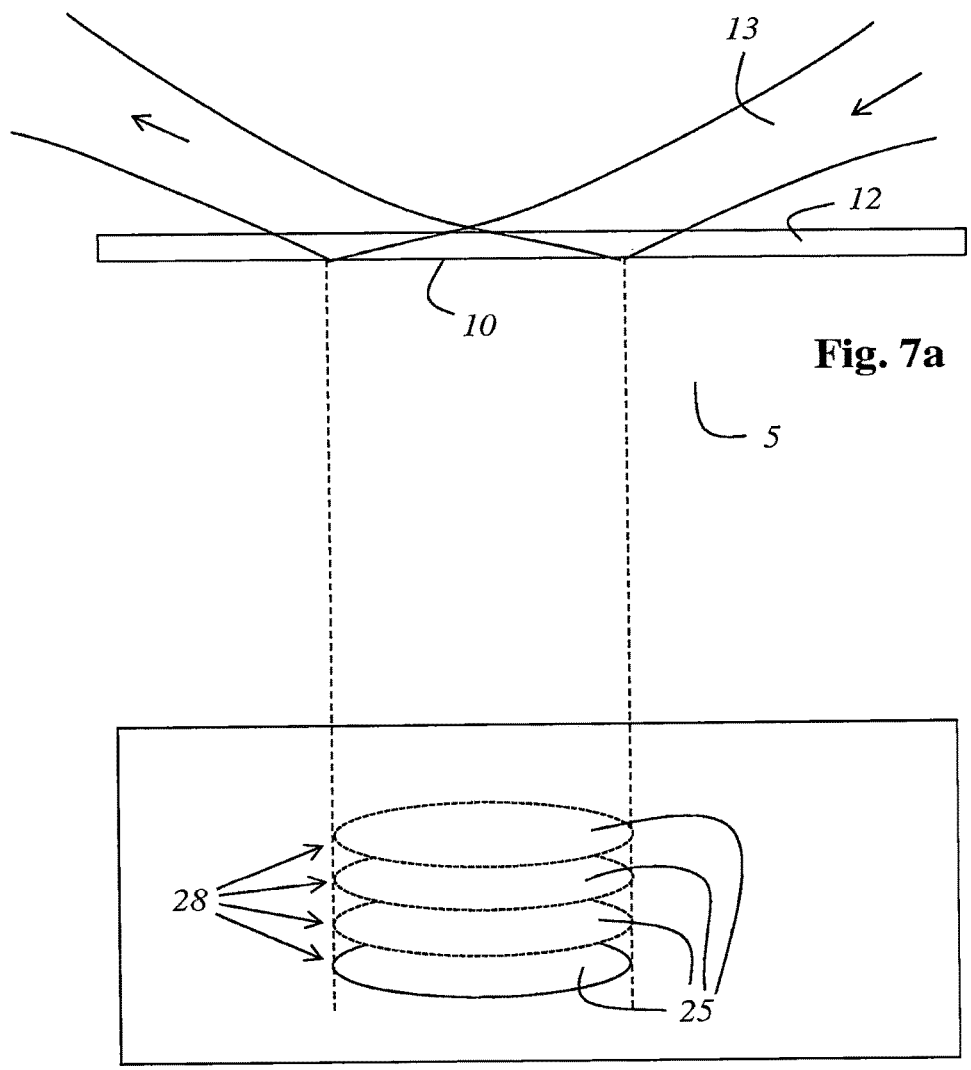

FIGS. 7a and 7b show a schematic depiction of the change of the site of impingement 28 of the illumination light bundle 13 onto the boundary surface 10 between the optically transparent medium 12 and the specimen 5.

By moving the specimen 5 relative to the illumination light bundle 13, for example, using an adjustable object stage, and/or by moving the illumination light bundle 13 relative to the specimen 5, for example, using a deflection means that is adjustable in terms of the deflection angle, and/or by moving the deflector 3, the site of impingement 28 can be successively changed, that is to say, the impingement surface 25 can be moved relative to the specimen. This is done, for instance, so as to acquire several two-dimensional images of different specimen regions, which can subsequently be combined to form a total image. For example, if the specimen 5 is moved perpendicular relative to the illumination light bundle 13 as seen from the drawing plane of FIG. 7a, the sites of impingement 28 as schematically shown in FIG. 7b can be lined up and a two-dimensional image can be generated for each site of impingement.

Figure 8:
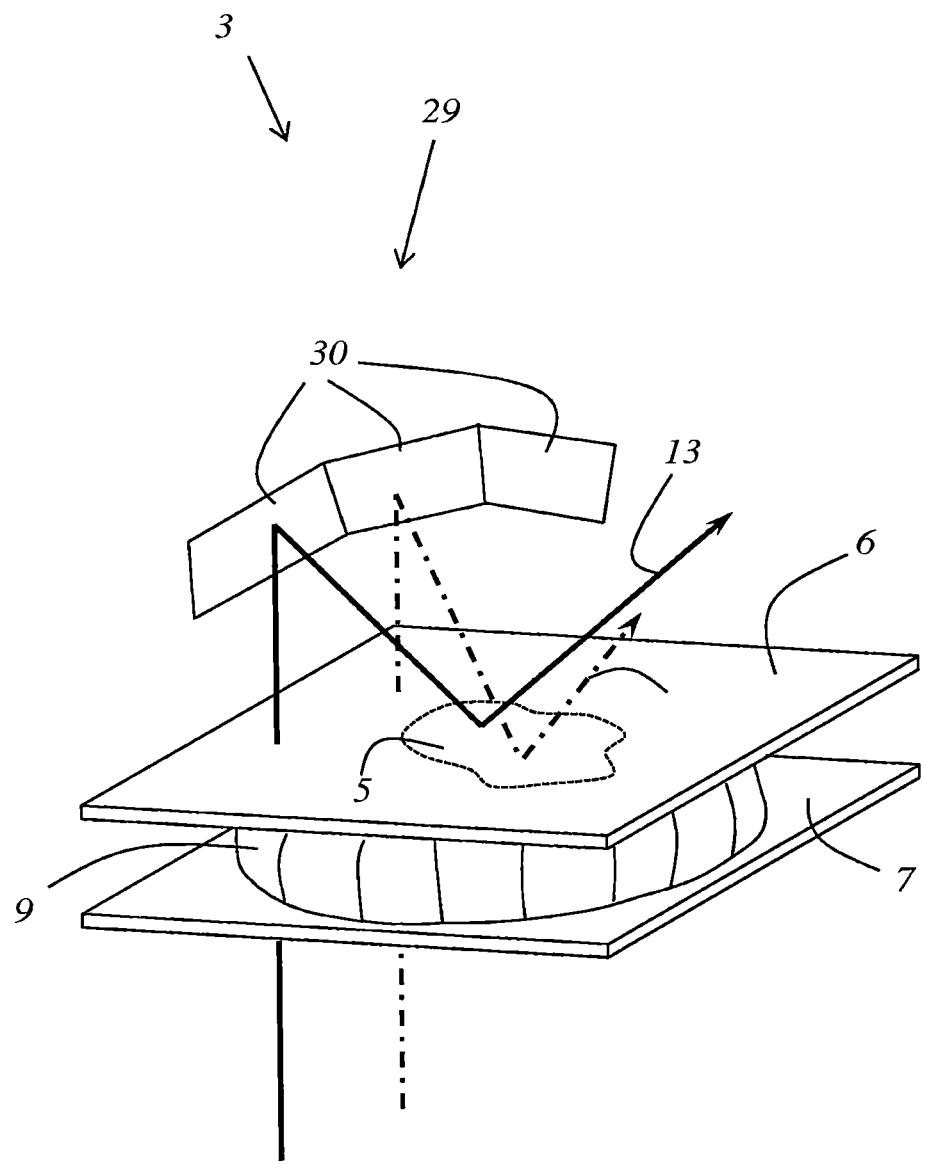

FIG. 8 shows a detailed view of an embodiment with a deflector 3 that has a facet mirror 29. The facet mirror 29 has several different facets with different spatial positions and orientations.

The specimen 5 that is to be examined is arranged in an aqueous nutrient medium 8 between a first cover glass 6 and a second cover glass 7. The cover glasses 6, 7 are sealed off with respect to each other by an encircling gasket 9 so that the aqueous nutrient medium 8 cannot escape.

In this embodiment, for example, by a beam deflector, the illumination light bundle 13 can be directed at different facets 30 so as to make the illumination light bundle 13 strike at different sites of impingement 28 and/or at different angles of incidence and/or with different directions of incidence of the illumination light bundle 13 onto the boundary surface 10 between the specimen 5 and the optically transparent medium 12, namely, the cover glass 6. As an alternative, instead of changing the spatial position and/or orientation of the illumination light bundle 13, it is also possible to move the facet mirror 29 relative to the illumination light bundle 13, for example, by means of a positioning unit.

Figure 9:
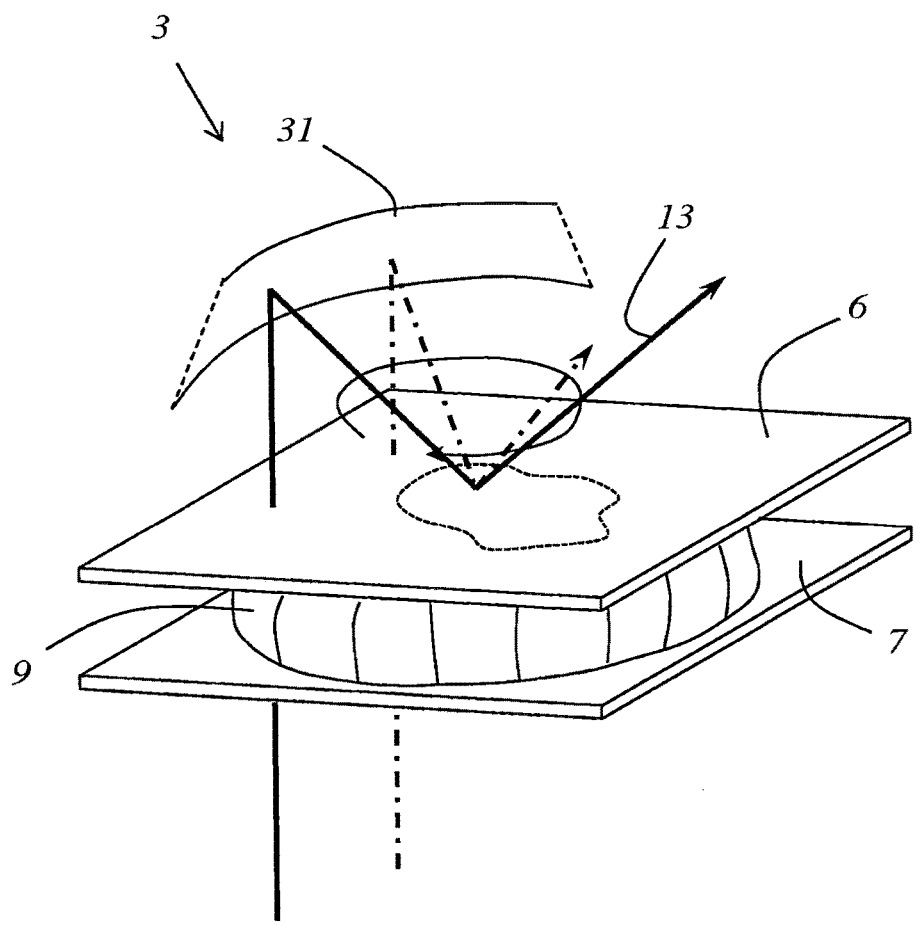

FIG. 9 shows a detailed view of an embodiment with a deflector 3 that has a frusto-conical mirror 31 of which, for the sake of greater clarity, only a section is shown.

The specimen 5 that is to be examined is arranged in an aqueous nutrient medium 8 between a first cover glass 6 and a second cover glass 7. The cover glasses 6, 7 are sealed off with respect to each other by an encircling gasket 9 so that the aqueous nutrient medium 8 cannot escape.

The frusto-conical mirror 31 makes it possible, for instance, to rotate the illumination light bundle 13 especially continuously and around an axis that runs through the site of impingement 28 so as to describe a conical surface.

Figure 10:
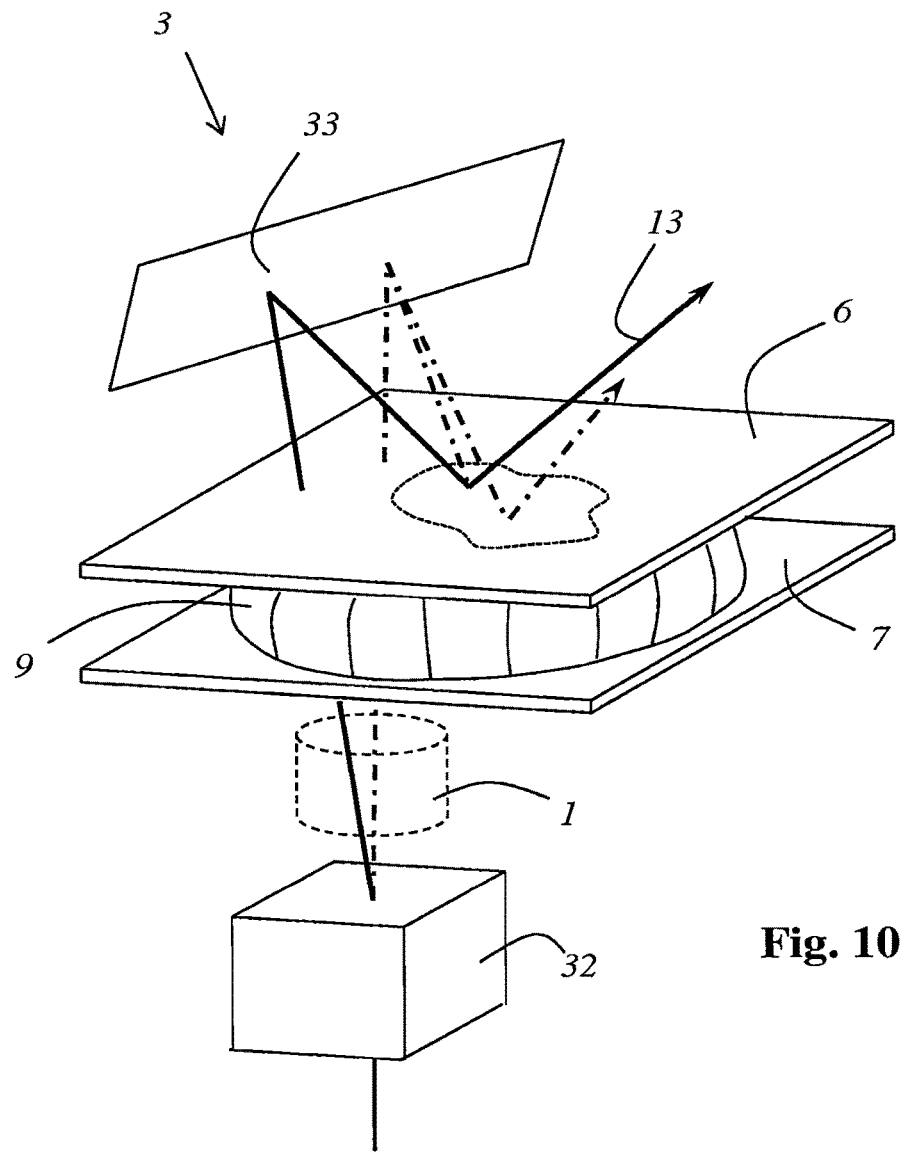

FIG. 10 shows a detailed view of an embodiment with a beam deflector 32 that is adjustable in terms of the deflection angle and that can comprise, for instance, several galvanometer mirrors in order to change the site of impingement 28 and/or the angle of incidence and/or the direction of incidence of the illumination light bundle 13 onto the boundary surface between the specimen 5 and the optically transparent medium 12, namely, the cover glass 6.

In this embodiment, the beam deflector 3 is configured as a flat mirror 33. By changing the site of impingement of the illumination light bundle 13 onto the flat mirror 33, it is possible to change the site of impingement 28 and/or the angle of incidence and/or the direction of incidence of the illumination light bundle 13 onto the boundary surface 10 between the specimen 5 and the optically transparent medium 12.

The illumination objective 1 and the course of the illumination light bundle 13 are only shown schematically in this figure and not shown completely corresponding to reality in order to illustrate the principle of the change of the illumination conditions.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS 1 illumination objective
2 detection objective
3 deflector
4 frusto-conical mirror surface
5 specimen
6 first cover glass
7 second cover glass
8 aqueous nutrient medium
9 gasket
10 boundary surface
11 immersion oil
12 optically transparent medium
13 illumination light bundle
14 detection light
15 reflective surface
16 outer surface
17 vessel
18 first deflector
19 other deflector
20 optically transparent medium
21 reflective surface
22 outer surface
23 second mirror surface
24 attachment means
25 impingement surface
26 large semi-axis
27 small semi-axis
28 site of impingement
29 facet mirror
30 facets
31 frusto-conical mirror
32 adjustable beam deflector
33 flat mirror

The invention claimed is:

1. A method for microscopic examination of a specimen, the method comprising:
    a. bringing the specimen into contact with an optically transparent medium that has a higher refractive index than the specimen,
    b. generating an illumination light bundle,
    c. directing the illumination light bundle through an illumination objective that focuses the illumination light bundle,
    d. deflecting the illumination light bundle that has passed through the illumination objective in the direction of the specimen that is to be examined, the deflecting being performed using a deflector arranged on a detection objective in such a way that the illumination light bundle strikes a boundary surface between the optically transparent medium and the specimen where the illumination light bundle is totally reflected for purposes of evanescently illuminating the specimen, and
    e. detecting fluorescent light that is emitted by the specimen and that passes through the detection objective,
    wherein:
        a. the specimen undergoes another examination in which its illumination is carried out with the illumination light bundle directly and without total reflection on the boundary surface,
        b. the specimen undergoes another examination in which its illustration for a SPIM examination (Single Plane Illumination Microscopy) is called out with the illumination light bundle directly and without total reflection on the boundary surface, and/or
        c. the specimen undergoes another examination in which its illumination is carried out with the illumination light bundle that has been shaped into a strip of light or quasi-strip of light, directly and without total reflection on the boundary surface, and
    wherein, for purposes of another examination, after the illumination light bundle has passed through the illumination objective, it is deflected onto the specimen by another deflector arranged on the illumination objective.

2. The method according to claim 1, wherein:
    a. the boundary surface between the specimen and the optically transparent medium is oriented at an angle that differs from zero relative to the optical axis of the illumination objective and/or of the detection objective, or
    b. the boundary surface between the specimen and the optically transparent medium is oriented perpendicular to the optical axis of the illumination objective and/or of the detection objective.

3. The method according to claim 1, wherein:
    a. after the illumination light bundle has been deflected, the illumination light bundle runs in a plane whose angle differs from zero relative to the optical axis of the illumination objective,
    b. the illumination light bundle is deflected in such a way that the illumination light bundle strikes the boundary surface between the specimen and the optically transparent medium at an angle of incidence within a range from 55° to 70°, and/or
    c. the illumination light bundle is deflected in such a way that the illumination light bundle strikes the boundary surface between the specimen and the optically transparent medium at an angle of incidence within the range from 60° to 64°.

4. The method according to claim 1, wherein:
    a. a site of impingement, an angle of incidence and/or a direction of incidence of the illumination light bundle onto the boundary surface between the specimen and the optically transparent medium is changed,
    b. the site of impingement, the angle of incidence and/or the direction of incidence of the illumination light bundle onto the boundary surface between the specimen and the optically transparent medium is changed continuously along a scanning path,
    c. the site of impingement, the angle of incidence and/or the direction of incidence of the illumination light bundle onto the boundary surface between the specimen and the optically transparent medium is changed by a beam deflector that is adjustable in terms of deflection angle and acts on the illumination light bundle, d. the site of impingement, the angle of incidence and/or the direction of incidence of the illumination light bundle onto the boundary surface between the specimen and the optically transparent medium is changed by moving the specimen relative to the illumination objective, e. the site of impingement, the angle of incidence and/or the direction of incidence of the illumination light bundle onto the boundary surface between the specimen and the optically transparent medium is changed by moving the deflector, and/or f. the deflector is configured as a mirror with multiple facets and the site of impingement, the angle of incidence and/or the direction of incidence of the illumination light bundle onto the boundary surface between the specimen and the optically transparent medium is changed in that different facets are illuminated consecutively.

5. The method according to claim 4, wherein:
a. a specimen region is associated with each site of impingement, and/or
b. a specimen region is determined for each site of impingement, taking into account an angle of incidence, a refractive index of the specimen, a refractive index of the optically transparent medium, a wavelength of the illumination light bundle and/or a diameter of the site of impingement.

6. The method according to claim 4, wherein an image, which was acquired by detection of the detection light emitted by the specimen during the illumination of each particular site of impingement, is associated with each site of impingement and/or with each associated specimen region.

7. The method according to claim 1, wherein a same site of impingement is illuminated consecutively from different directions.

8. The method according to claim 1, wherein a cross section of the illumination light bundle is circular, or the illumination light bundle is in a form of a strip of light or a quasi-strip of light.

9. The method according to claim 1, wherein the optical axis of the illumination objective and the optical axis of the detection objective are oriented parallel or coaxially to each other, and/or the detection objective and the illumination objective face in opposite directions and are arranged opposite from each other.

10. The method according to claim 1, wherein the illumination light bundle is coupled into the illumination objective in such a way that it runs off-center through the illumination objective.

11. A device for microscopic examination of a specimen in which the specimen is brought into contact with an optically transparent medium that has a higher refractive index than the specimen, the device comprising:
an illumination objective configured to focus an illumination light bundle;
a detection objective on which a deflector is arranged so as to deflect the illumination light bundle which has passed through the illumination objective onto a boundary surface between the optically transparent medium and the specimen; and
a beam deflector that is adjustable in terms of deflection angle for purposes of changing a site of impingement, an angle of incidence and/or a direction of incidence of the illumination light bundle onto the boundary surface.

12. The device according to claim 11, wherein the optically transparent medium is the deflector or part of the deflector.

13. The device according to claim 11, wherein:
a. the deflector has a block made of transparent material,
b. the deflector is coupled directly to a front lens of the detection objective, or the deflector comprises a front lens of the detection objective,
c. the deflector has the block made of transparent material and at least one outer surface of the block is configured as a mirror, and/or
d. the deflector has the block made of transparent material and one outer surface of the block is configured and arranged as a window for coupling in the illumination light bundle.

14. The device according to claim 11, further comprising another deflector, wherein:
a. the another deflector is configured for another examination in which the specimen is illuminated with the illumination light bundle directly and without total reflection on the boundary surface, and/or
b. the another deflector is arranged on the detection objective for another examination in which the specimen is illuminated with the illumination light bundle directly and without total reflection on the boundary surface.

15. The device according to claim 11, wherein:
a. the deflector or another deflector is configured as a mirror or as a facet mirror, or
b. the deflector or another deflector has at least one mirror or a facet mirror, and/or
c. the deflector or another deflector has a mirror with a frusto-conical mirror surface.

16. The device according to claim 11, wherein the deflector and/or another deflector are arranged movably on the detection objective.

17. A method for microscopic examination of a specimen, the method comprising:
a. bringing the specimen into contact with an optically transparent medium that has a higher refractive index than the specimen,
b. generating an illumination light bundle,
c. directing the illumination light bundle through an illumination objective that focuses the illumination light bundle,
d. deflecting the illumination light bundle that has passed through the illumination objective in the direction of the specimen that is to be examined, the deflecting being performed using a deflector arranged on a detection objective in such a way that the illumination light bundle strikes a boundary surface between the optically transparent medium and the specimen where the illumination light bundle is totally reflected for purposes of evanescently illuminating the specimen,
e. using a beam deflector that is adjustable in terms of deflection angle so as to change a site of impingement, an angle of incidence and/or a direction of incidence of the illumination light bundle onto the boundary surface, and
f. detecting fluorescent light that is emitted by the specimen and that passes through the detection objective.

* * * * *